United States Patent

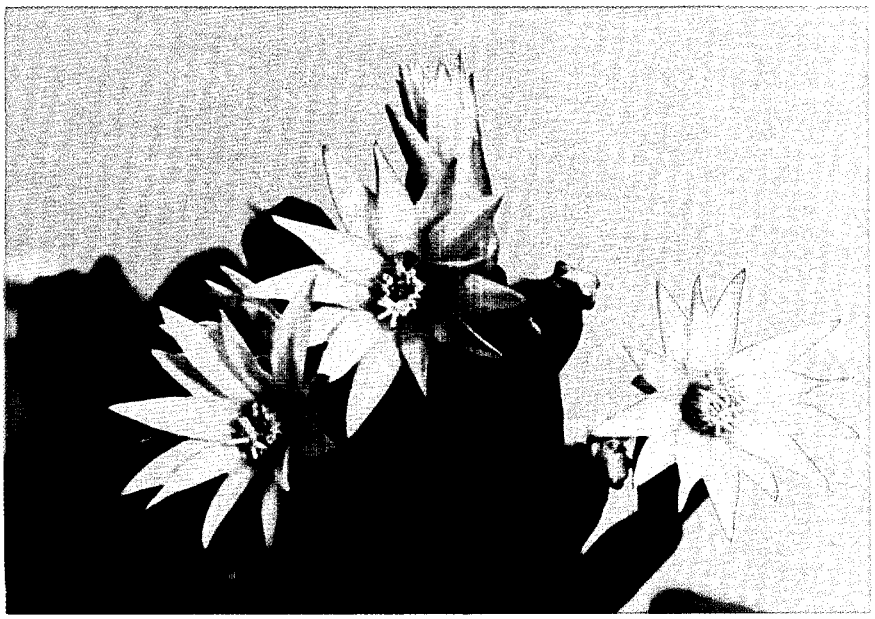

Plant Pat. 3,954
Patented Oct. 12, 1976

3,954

EASTER CACTUS

Joseph Harry Johnson, Sr., Fallbrook, Calif., assignor to Ethan M. Johnson, doing business as Johnson Cactus Gardens, Fallbrook, Calif.

Filed Mar. 17, 1975, Ser. No. 558,707
Int. Cl.[2] A01H 5/00
U.S. Cl. Plt.—88 1 Claim

ABSTRACT OF THE DISCLOSURE

An Easter cactus characterized by the Tyrian Pink color of its blooms, by its upright habit, and by its free flowering propensity.

BRIEF SUMMARY OF THE INVENTION

My invention relates to a new and distinct variety of Easter cactus.

My new Easter cactus is shown in the color photograph. I produced this variety by hybridization. Easter cactus is a group of hybrids known in the horticultural world and the nursery trade by that name. The name "Easter cactus" is derived from this group's habit of flowering during the Easter period, or April–May. The group Easter cactus as a whole are derived from hybrids with *Epiphyllopsis gaertneri.*

DESCRIPTION

The following is a description of my new and distinct variety of Easter cactus:

(a) Plant family: Cactaceae.
(b) Subtribe: Epiphyllanae.
(c) Genera involved: Rhipsalidopsis (Britton & Rose) and Epiphyllopsis (Lemaire).
(d) Species involved: *Rhipsalidopsis rosea* (Lagerheim) and *Epiphyllopsis gaertneri* (Regel) Berger.
(e) Horticultural hybrids involved: China Rose and Peter pan.
(f) General: Spineless, epiphytic (but equally able to grow in rich humus soil mixtures); flattened stems (occasionally triangular), divided into short joints from 3.5 to 7 cm. long, averaging 4 cm., and from 2–3.5 cm. broad, often with tufts of brownish bristles, 5–7 mm. long, at the joints; occasional yellowish bristles seen at the areoles or indentations along the margins;

dichotomous branching with one to several branches at each joint; upright habit with some spreading; stems grass-green; stem-joint green with purplish crenate margins; and fruit unknown. Flowers terminal, monochromic, regular, rotate with very short tube; one to several flowers at the tip; buds fusiform, 2.5–3 cm. in length at maturity; perianth segments lanceolate, 2.5–3 cm. long in several series, almost all petaloid; anthers yellow with purplish filaments, included; pistil light yellow, 5-lobed, exceeding the stamens; flowers opening to 4 to 5 cm. across rotate, perianth segments Tyrian Pink (Ridgway Plate XII); flowering April–May under natural conditions in California.

(g) The principal distinguishing characteristic of the new and distinct variety of Easter cactus is its color, which is Tyrian Pink (Ridgway, Plate XII, Color Standards and Color Nomenclature, by Robert Ridgway, Washington, D.C., 1912). Additional distinguishing features are its upright habit and free flowering propensity.

| | *Schlumbergera Rhipsalidopsis Epiphyllopsis gaertneri* | *Rhipsalidopsis rosea* | Rhipsalidopsis hybrid, China Rose | Rhipsalidopsis hybrid, Peter Pan | Shocking Pink | Haage P. 154, *Rhipsaphyllopsis graeseri* |
|---|---|---|---|---|---|---|
| Flower color | Dark scarlet | Rose | Deep rose-pink | Crimson | Pink (Tyrian) | Given as shades of red. |
| Flower size | 3–4 cm. broad (rotate). | 3–3.7 cm. broad (rotate). | 3–3.5 cm. broad (rotate). | 1 cm. broad (tubular). | 4–5 cm. broad (rotate). | Given as similar in size to Rhipsalidopsis. |
| Stem-joint (leaf) size | 5 cm. long, 2 cm. broad. | 2–3 cm. long, 0.5–1 cm. broad. | 3–4 cm. long, 2 cm. broad. | 2–3 cm. long, 1–2 cm. broad. | 3.5–7 cm. long, 2–3.5 cm. broad. | ? |
| Stem-joint | Green with purplish crenate margins. | Green-reddish in full light. | Green, crenate margin. | Green, smooth margins. | Green with purplish crenate margins. | ? |
| Stem-joint | Flat, occasionally angled. | Strongly 4-angled, occasionally flat. | Flat | Flat | Flat, very occasionally angled. | ? |
| Flower style | Red | Rose-red | Yellow | Yellow | Yellow | ? |
| Fruit | Red, 15 mm. long | Yellowish | Yellow, 12–15 cm. long. | Yellow, 12 cm. long. | Unknown | ? |
| Bristles in aeroles | Few, yellowish | Occasional | None | None | Occasional yellowish bristles. | ? |

PARENTAGE

My new and distinct variety of Easter cactus is a selected seedling from cross-hybridization made as follows: (1) Rhipsalidopsis (Britton & Rose) hybrid China Rose, by (2) Rhipsalidopsis (Britton & Rose) hybrid Peter Pan.

Rhipsalidopsis: see the description for the genus Rhipsalidopsis and *Rhipsalidopsis rosea* (Lagerheim) in The Cactaceae, by N. L. Britton and J. N. Rose. This was published in four volumes bound as two volumes by Dover Publications, Inc., New York. It was originally published as Publication No. 248 of the Carnegie Institution of Washington. The Library of Congress Catalog Card Number is 63–17924.

Rhipsalidopsis hybrid China Rose and Peter Pan are listed in the commercial catalog of Johnson Cactus Garden, 2735 Olive Hill Road, Fallbrook, Calif. 92028. The two hybrids China Rose and Peter Pan are complex hybrids that I previously hybridized and propagated from *Rhipsalidopsis rosea* and *Schlumbergera gaertneri* (Regel), Britton and Rose (or *Rhipsalidopsis gaertneri*).

PROPAGATION

I propagated the plant asexually by stem-joint cuttings in a peat moss medium. Commercially plants may be propagated in such a medium in commercial flats. Joints may be detached whole without cutting merely by twisting or pinching at the constriction. The joints are then inserted into the proper medium, peat moss, sphagnum moss, etc., to a depth of ¼–½ inch. New roots will form at the severed or detached surface.

I claim:

1. A new and distinct variety of Easter cactus substantially as shown and described, characterized by the Tyrian Pink color of its blooms, by its upright habit, and by its free flowering propensity.

References Cited

Cacti and Succulents, Haage, 1963, E. P. Dutton & Co., Inc., New York, N.Y., pp. 151, 152 and 154 relied on.

ROBERT E. BAGWILL, Primary Examiner